United States Patent [19]
Ferrara

[11] 4,131,549
[45] Dec. 26, 1978

[54] SERUM SEPARATION DEVICE
[76] Inventor: Louis T. Ferrara, 2988-Ave. T, Brooklyn, N.Y. 11229
[21] Appl. No.: 797,357
[22] Filed: May 16, 1977
[51] Int. Cl.² .................. B01D 33/00; A61B 5/14
[52] U.S. Cl. .............................. 210/359; 128/2 F; 210/518; 210/DIG. 23
[58] Field of Search ............ 128/2 F, 214 C, 272, 128/DIG. 5; 210/83, 359, 516, 518, DIG. 23, DIG. 24

[56] References Cited
U.S. PATENT DOCUMENTS

| | | | |
|---|---|---|---|
| 3,765,402 | 10/1973 | Grabhorn | 128/2 F |
| 3,800,947 | 4/1974 | Smith | 210/DIG. 23 |
| 3,814,079 | 6/1974 | LeRoy, Sr. | 210/DIG. 23 |
| 3,877,465 | 4/1975 | Miyake | 128/2 F |
| 3,894,952 | 7/1975 | Ayres | 210/DIG. 23 |
| 3,965,889 | 6/1976 | Sachs | 128/2 F |
| 3,969,250 | 7/1976 | Farr | 210/359 |

Primary Examiner—Robert H. Spitzer

[57] ABSTRACT
The invention relates to the collection of blood with the subsequent separation of serum after clotting for use in chemical analysis thereof. The device is used within an evacuated blood collection tube system in which the latter has a stopper to seal said tube from outside environment and to preserve the systems vacuum. This tube or system is used in conjunction with a special holder and specially designed two ended needle. The needle is threaded into one end of the holder allowing one end to exist within the confines of the holder. The evacuated tube is placed in said holder and after vena puncture is accomplished the tube is pressed forward thereby puncturing the rubber stopper and penetrating said stopper allows blood to enter the evacuated system. Within the glass tube is a plastic cylinder or tubular element in which the aforementioned blood being guided into this element or cylinder is allowed to clot when the serum is allowed to pass through a filter by the force of gravity and or centrifugation whereby said serum becomes located outside of said tubular element and finally being located within the confines of the glass tube. The tubular element is discarded along with the clot and cellular elements contained therein.

2 Claims, 4 Drawing Figures

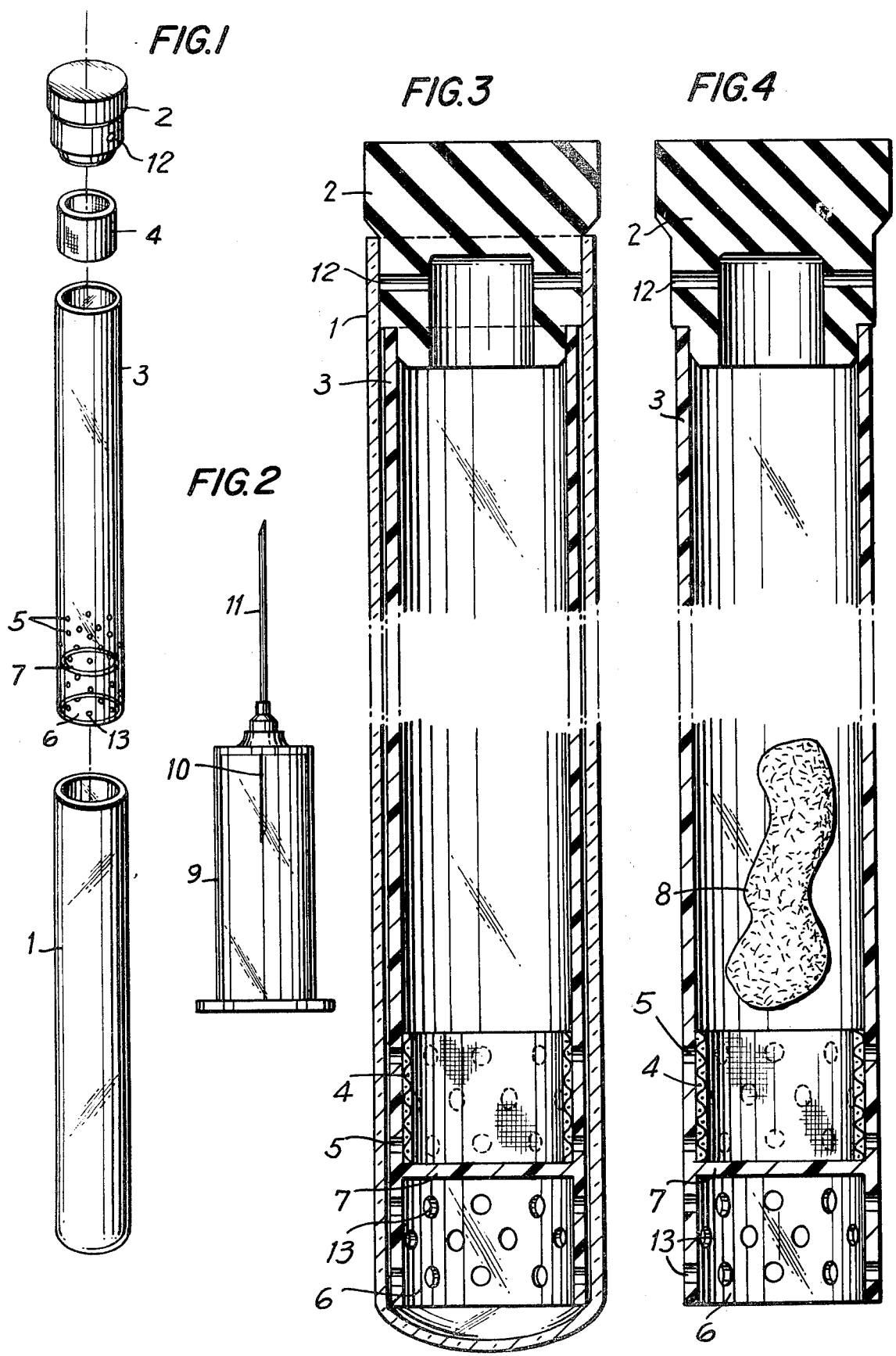

SERUM SEPARATION DEVICE

PRIOR ART

Prior to this invention blood has been collected as described and allowed to clot. After clotting the serum has been aspirated or carefully poured into another tube to await chemical analysis. In more recent times jell-like substances having intermediate specific gravities have been placed at the bottom of these collection systems thereby acting as barriers between clot and serum after centrifugation. Subsequently the serum may be poured off into another container or possibly used in an automated system whereby the serum is aspirated off. Other inventions use this type of barrier substance in conjunction with a cup, the latter forming a hard surface to act as a wall which would allow an aspirating probe to aspirate serum without the hinderance of being clogged by the jell-like material. The Adler device U.S. Pat. No. 3,929,646 has a cup-like device used in conjunction with such jell-like material the latter being used to recover most of the serum and act to seal and hold said cup in place.

These inventions suffer disadvantages in that serum must either be poured off into another container for subsequent use or aspirated while clot and cellular materials remain in the tube seperated by barriers of sorts. The Adler device suffers in that vent holes can become clogged during blood withdrawal and can also be penetrated by the gell-like material thereby defeating its purpose of presenting a hard and clear of gell surface to a probe which is to aspirate the serum without being clogged. It is also possible for the cup to be jared by a pipet and thereby mixing cellular elements and serum.

It is with this in mind that the present invention, being a modification of another invention submitted by this inventor Ser. No. 633,399 Nov. 19, 1975, eliminates the gell-like barriers and allows serum to be seperated and segragated completely from the system from its clot and cellular elements. In other words the invention comprises a system free of gell-like barriers and the like and eliminates any pouring into another container with the subsequent re-identification of this other container. One ends up with a glass tube containing only serum which can be used in an automated system of probe aspiration or pipetted manually. The system also has the advantages of the gell-like material in that substantially all the serum is recovered. It is unlike similar inventions using a filter device which will not recover all the serum due to interference of the clot as the filter approaches it and is stopped by the opposing force of the clot.

SUMMARY OF INVENTION

In a preferred embodiment of the invention there is provided a blood serum seperation unit which includes a tubular structure opened at both ends. At one end of this tubular structure is fitted permanently a stopper having the resiliency or quality of rubber which is self-sealing. The bottom end of this tubular element which is opposite to the location of the stopper, is fitted with a filter device supported by the walls of the tubular structure and a base which is an integral part of the tubular structure. There are provided, immediately adjacent to the filter, multiple openings on the walls of the tubular structure thereby circumventing said wall and providing passageways for serum to be filtered through. The entire tubular structure which in essence consists of a stopper at one end and filter device at the other end, being substantially shorter in length and smaller in diameter slides into or is received by another tubular element preferrably of glass construction. In essence there exists a tube within a tube, whereby the inner tubular structure preferably of plastic construction with its attached stopper seals the entire system from the outside enviornment. When the entire system being evacuated of air is placed in a special holder containing a double ended needle it is ready to operate. Venapuncture is made and the opposite end of the special needle penetrates the stopper allowing blood to enter into the inner tubular structure containing the filter device at the bottom. After clotting, centrifugation causes serum to be filtered or forced through the pores of the filter device and through the multiple openings and thereby finding storage in space provided below and to the sides of the entire tubular structure. That is to say that the serum finds its way out of the plastic tubular structure containing the filter and is stored within the confines of the glass or outer tubular element. The clot and cellular material being confined or isolated within the inner tubular structure is totally removed and discarded thereby leaving the outer glass tube or tubular element with the needed serum contents.

BRIEF EXPLANATION OF DRAWING

FIG. 1 illustrates an exploded view of a typical preferred embodiment of the invention.

FIG. 2 illustrates a holder with attached two-ended needle used to support or receive the entire blood collection system prior to venapuncture.

FIG. 3 illustrates the embodiment of FIG. 1 shown in a side cross-section view taken along the elongated longitudinal axis thereof.

FIG. 4 illustrates also in cross-section through the inner and withdrawn tube the inner tube of the FIG. 1 embodiment with the clot as it would appear after centrifugation.

DETAILED DESCRIPTION OF THE INVENTION

FIGS. 1, 3, and 4 represent a common embodiment of the invention. Tubular element 3, being the inner of the two tubular structures is fitted at one end with stopper 2. Said stopper being provided with air vent 12 is used to provide means of sealing the system from the outside enviornment and a means to allow blood to enter the system by needle penetration.

A filter device 4 constructed in a tubular fashion is permanently placed at one end of tube 3 at base 7 whereby plural openings 5 are provided immediately adjacent to said filter to allow serum to pass through and be stored in spaces within the outer tube 1.

The filter device 4 is of such porosity that serum is allowed to pass through while holding back clot and cellular material. Since blood cells range in size from approxamately 7-12 microns a filter pore size substantially less than 7 microns must be used. Such filters are manufactured by Gelman, and spectrum Medical Industries and are of the polycarbonate and cellulosic membrane types.

FIG. 3 illustrates the invention as it would normally appear prior to venapuncture. Tubular element 3 is shown as being contained in outer tubular element 1. Vent hole 12 is used to allow air to escape during the evacuation process, and this vent is sealed off by the wall of the outer tube when the stopper is pressed or forced in place after evacuation. At the bottom of element 3 is a solid circular base 7 which is an integral part of said tubular element 3. This base supports the filter at the bottom so that the force of centrifugation does not tear or rupture the filter membrane. This base 7 is provided with plural openings 5 which allow serum to pass from the filter into spaces 6 below element 3, and spaces within tubular element 1. In this respect it is pointed out that tubular element 3 must fit tube 1 in such a manner that adequate or substantial space is provided for serum to be stored inbetween the outer walls of tube 3 and inner walls of tube 1.

FIG. 4 illustrates the invention as it would appear after centrifugation. Stopper 2 is permanently affixed to tube 3 and in so being provides a means to withdraw tube 3 with its contents, clot 8 and other cellular material not shown in drawing.

FIG. 4 is illustrative therefore of how the invention would appear after centrifugation and subsequent removal from within the confines of tubular element 1.

The entire operation of the system in its preferred embodiment operates as follows:

The assembled blood collection unit as illustrated in the cross-sectional enlargement FIG. 3 is inserted within tube holder 9 stopper 2 first so that said stopper 2 comes in contact with needle end 10. When venapuncture is initiated using end of needle 11 the entire blood collection unit is pressed foward towards end of needle 10 so that said needle penetrates stopper 2. Since the system has previously been evacuated of air blood flows and fills the spaces within tubular element 3 which contains filter 4. Filter 4 incidentally is sealed to the walls of tubular element 3 in such a manner that blood cannot leak from inbetween its outer wall and the adjacent inner wall of said element 3. After venapuncture is completed, i.e., needle withdrawn from vein, the entire blood collection tube FIG. 3 is removed from said holder FIG. 2, and the blood within tubular element 3 is allowed to clot. In this regard a clot enhancer such a microscopic glass particles or Kaolin may be added to the inside wall of tubular element 3 in order to shorten clotting time. When clotting is complete, the entire collection system FIG. 3 is placed in a centrifuge, stopper up and centrifuged.

During centrifugation all material within tubular element 3 is forced downward. The blood clot and cellular elements being heavier than the serum portion of the blood reach the bottom of tubular element 3 and tend to come to rest on base 7. The serum portion, although of lesser specific gravity than the clot and cellular material would ordinarily remain above the clot and cellular material. However since a force does exist upon the serum it is forced downwardly and finds its way through the filter pores of filter 4, and through the multiple openings 5, which surround the wall of the filter. These multiple openings are below the filter appearing as part of base 7 FIG. 1 and also adjacent to said filter in circumferential orientation as part of tubular element 3. The serum thus finds its way into spaces between the outer wall of element 3 and inner wall of element 1. In essence the serum is stored in spaces within tubular element 1. The clot and cells which are considerably larger than the pores of filter 4 are during the centrifugal proccess left behind and in essence remain in tubular element 3 for storage and subsequent removal. At this point one grasps stopper 2 and removes it from the system. Attached to said stopper is tubular element 3 with its contents as shown in FIG. 4. This is then discarded since it is of no interest or use. One is left with tubular element 1 containing the needed portion of blood, i.e. serum. There is no need to transfer the needed serum to another tube and hence no need to further identify the specimen. The patients name and identification appear on the original collection tube and any subsequent numbering as is customary appears on this tube.

I claim:

1. A serum separation device comprising, in combination:

a first elongated tubular vessel closed at the bottom or lower end and open at the top or upper end;

a resilient stopper with air vents being permanently affixed to said top end, said air vents being above the connection between the stopper and the first vessel top end to allow the first vessel interior to be vented;

a filter means being contained within the first vessel lower end and communicating with the exterior of said first vessel through the sidewall thereof, said filter means being of a size so that only serum can pass therethrough;

a second elongated tubular vessel closed at the bottom or lower end and open at the top or upper end and being substantially longer in length and larger in diameter than said first vessel; and, said first vessel being telescopingly receivable by said second vessel so that a space is formed between the two vessels, said resilient stopper including means to intermittently seal the second vessel upper end and being adapted to receive a cannula intermittently so that blood from a subject can be directed into said first vessel;

whereby, said blood is allowed to clot and may be separated by centrifugal means to cause said serum to pass through the filter means and be stored in said space while clot and cellular material remain within the first vessel.

2. A serum separating device as described in claim 1, whereby the tubular vessels having been placed in a stopper-up position allows serum to be separated from cellular and coagulant material by centrifugal forces and said filter means; and thus, having separated and stored said serum within the space formed by the first and second vessels the resilient stopper with the permanently affixed first vessel may be disengaged or disloged from the opened end of the second tubular vessel and discarded leaving the second vessel with the needed serum.

* * * * *